United States Patent
Bruneau et al.

(10) Patent No.: US 8,348,977 B2
(45) Date of Patent: *Jan. 8, 2013

(54) ARTIFICIAL SPINOUS PROCESS FOR THE SACRUM AND METHODS OF USE

(75) Inventors: Aurelien Bruneau, Jacksonville, FL (US); Thomas A. Carls, Memphis, TN (US); Eric C. Lange, Pleasanton, CA (US); Kent M. Anderson, Mountain View, CA (US); Jean Taylor, Cannes (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 131 days.

This patent is subject to a terminal disclaimer.

(21) Appl. No.: 12/827,248

(22) Filed: Jun. 30, 2010

(65) Prior Publication Data
US 2010/0268277 A1 Oct. 21, 2010

Related U.S. Application Data

(63) Continuation of application No. 11/341,178, filed on Jan. 27, 2006, now Pat. No. 7,837,711.

(51) Int. Cl.
*A61B 17/70* (2006.01)
(52) U.S. Cl. .................. 606/248; 606/249; 606/280
(58) Field of Classification Search .......... 606/60, 606/246, 248, 249, 286
See application file for complete search history.

(56) References Cited

U.S. PATENT DOCUMENTS

| | | | |
|---|---|---|---|
| 2,677,369 A | 5/1954 | Knowles | |
| 3,648,691 A | 3/1972 | Lumb et al. | |
| 4,011,602 A | 3/1977 | Rybicki et al. | |
| 4,257,409 A | 3/1981 | Bacal et al. | |
| 4,554,914 A | 11/1985 | Kapp et al. | |
| 4,573,454 A | 3/1986 | Hoffman | |
| 4,604,995 A | 8/1986 | Stephens et al. | |
| 4,686,970 A | 8/1987 | Dove et al. | |
| 4,827,918 A | 5/1989 | Olerud | |
| 5,000,165 A | 3/1991 | Watanabe | |
| 5,011,484 A | 4/1991 | Breard | |
| 5,047,055 A | 9/1991 | Bao et al. | |

(Continued)

FOREIGN PATENT DOCUMENTS
DE 2821678 A1 11/1979
(Continued)

OTHER PUBLICATIONS

"Dispositivo Intervertebrale Ammortizzante DIAM," date unknown, p. 1.

(Continued)

*Primary Examiner* — Eduardo C Robert
(74) *Attorney, Agent, or Firm* — Dilworth & Barrese, LLP

(57) ABSTRACT

Devices and methods for attaching a support to the sacrum. One device may include first and second anchors that mount to the sacrum, and first and second lateral extensions coupled to the anchors to secure the device to the sacrum. A bearing face having a width is positioned between the lateral extensions. The face may have a height in an anterior-posterior direction greater than the spinous process of the sacrum. Further, the bearing face may be oriented in a superior direction when the device is mounted to the sacrum. An implant may be supported by the device to space the sacrum and L5 vertebra. The implant may be an interspinous device and positioned between the L5 spinous process and the bearing face. The implant is supported at least in part by the bearing face.

17 Claims, 4 Drawing Sheets

U.S. PATENT DOCUMENTS

| | | |
|---|---|---|
| 5,092,866 A | 3/1992 | Breard et al. |
| 5,133,717 A | 7/1992 | Chopin |
| 5,201,734 A | 4/1993 | Cozad et al. |
| 5,306,275 A | 4/1994 | Bryan |
| 5,360,430 A | 11/1994 | Lin |
| 5,366,455 A | 11/1994 | Dove |
| 5,415,659 A | 5/1995 | Lee et al. |
| 5,415,661 A | 5/1995 | Holmes |
| 5,437,672 A | 8/1995 | Alleyne |
| 5,454,812 A | 10/1995 | Lin |
| 5,496,318 A | 3/1996 | Howland et al. |
| 5,609,634 A | 3/1997 | Voydeville |
| 5,628,756 A | 5/1997 | Barker, Jr. et al. |
| 5,645,599 A | 7/1997 | Samani |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,068,630 A | 5/2000 | Zucherman et al. |
| 6,132,464 A | 10/2000 | Martin |
| 6,293,949 B1 | 9/2001 | Justis et al. |
| 6,352,537 B1 | 3/2002 | Strnad |
| 6,364,883 B1 | 4/2002 | Santilli |
| 6,402,750 B1 | 6/2002 | Atkinson et al. |
| 6,440,169 B1 | 8/2002 | Elberg et al. |
| 6,451,019 B1 | 9/2002 | Zucherman et al. |
| 6,500,178 B2 | 12/2002 | Zucherman et al. |
| 6,514,256 B2 | 2/2003 | Zucherman et al. |
| 6,520,990 B1 | 2/2003 | Ray |
| 6,582,433 B2 | 6/2003 | Yun |
| 6,626,944 B1 | 9/2003 | Taylor |
| 6,645,207 B2 | 11/2003 | Dixon et al. |
| 6,695,842 B2 | 2/2004 | Zucherman et al. |
| 6,709,435 B2 | 3/2004 | Lin |
| 6,723,126 B1 | 4/2004 | Berry |
| 6,733,534 B2 | 5/2004 | Sherman |
| 6,761,720 B1 | 7/2004 | Senegas |
| 6,835,205 B2 | 12/2004 | Atkinson et al. |
| 6,946,000 B2 | 9/2005 | Senegas et al. |
| 7,041,136 B2 | 5/2006 | Goble et al. |
| 7,048,736 B2 | 5/2006 | Robinson et al. |
| 7,087,083 B2 | 8/2006 | Pasquet et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,445,637 B2 | 11/2008 | Taylor |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0097931 A1 | 5/2004 | Mitchell |
| 2004/0133280 A1 | 7/2004 | Trieu |
| 2004/0199255 A1 | 10/2004 | Mathieu et al. |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0129239 A1 | 6/2006 | Kwak |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241610 A1 | 10/2006 | Lim et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0043362 A1 | 2/2007 | Malandain et al. |
| 2007/0100340 A1 | 5/2007 | Lange et al. |
| 2007/0123861 A1 | 5/2007 | Dewey et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0198091 A1 | 8/2007 | Boyer et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0140082 A1 | 6/2008 | Erdem et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2010/0121379 A1 | 5/2010 | Edmond |

FOREIGN PATENT DOCUMENTS

| | | |
|---|---|---|
| EP | 0322334 B1 | 2/1992 |
| EP | 1138268 A1 | 10/2001 |
| EP | 1330987 A1 | 7/2003 |
| EP | 1854433 A1 | 11/2007 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799948 A1 | 4/2001 |
| FR | 2816197 A1 | 5/2002 |
| FR | 2884135 A1 | 4/2005 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |
| WO | WO 2006/110578 A2 | 10/2006 |
| WO | WO 2007/034516 A1 | 3/2007 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Aota et al., "Postfusion Instability at the Adjacent Segments After Rigid Pedicle Screw Fixation for Degenerative Lumbar Spinal Disorders," J. Spinal Dis., Dec. 1995, pp. 464-473, vol. 8, No. 6.

Benzel et al., "Posterior Cervical Interspinous Compression Wiring and Fusion for Mid to Low Cervical Spinal Injuries," J. Neurosurg., Jun. 1989, ppp. 893-899, vol. 70.

Booth et al., "Complications and Predictive Factors for the Successful Treatment of Flatback Deformity (Fixed Sagittal Imbalance)," SPINE, 1999, pp. 1712-1720, vol. 24, No. 16.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al , "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al , "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al , "Development and Preclinical Testing of a New Tension-Band Device for the Spine: the Loop System," Eur, Spine J , Aug. 7, 2002, pp. S186-S191 vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-6.79, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rahm et al., "Adjacent-Segment Degeneration After Lumbar Fusion with Instrumentation—A Retrospective Study," J. Spinal Dis., Oct. 1996, pp. 392-400, vol. 9, No. 5.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schären et al, "Erfolge and Probleme langstreckiger Fusionen der degenerativen Lendenwirbelsäule," Osteosynthese International, Jul. 17, 1998, pp. 173-179, vol. 6, Johann Ambrosius Barth.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "Lumbar Motion Segment Pathology Adjacent to Thoracolumbar, Lumbar, and Lumbosacral Fusions," SPINE, Apr. 15, 1996, pp. 970-981, vol. 21, No. 8.

Schlegel et al., "The Role of Distraction in Improving the Space Available in the Lumbar Stenotic Canal and Foramen," SPINE, 1994, pp. 2041-2047, vol. 19, No. 18.

Senegas et al , "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maêtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation,Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167 176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel , ed., Jun. 1994, pp. 116-123, vol. 6, No. 2.

Wittenberg et al., "Flexibility and Distraction after Monosegmental and Bisegmental Lumbrosacral Fixation with Angular Stable Fixators," SPINE, 1995, pp. 1227-1232, vol. 20, No. 11.

Zdeblick et al., "Two-Point Fixation of the Lumbar Spine Differential Stability in Rotation." SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

ARTIFICIAL SPINOUS PROCESS FOR THE SACRUM AND METHODS OF USE

REFERENCE TO RELATED APPLICATION

This application is a continuation of U.S. patent application Ser. No. 11/341,178, filed Jan. 27, 2006, now U.S. Pat. No. 7,837,711 B2, the contents of which are hereby incorporated herein by reference in its entirety.

BACKGROUND

The present application is directed to devices to mount with the sacrum, and more specifically to devices that attach to the sacrum and provide a support for positioning an implant between the sacrum and fifth lumbar vertebra.

The spine is divided into regions that include the cervical, thoracic, lumbar, and sacrococcygeal regions. The cervical region includes the top seven vertebrae identified as C1-C7. The thoracic region includes the next twelve vertebrae identified as T1-T12. The lumbar region includes five vertebrae L1-L5. The sacrococcygeal region includes nine fused vertebrae comprising the sacrum comprising S1-S5 vertebrae and four or five rudimentary members that form the coccyx.

The sacrum is shaped like an inverted triangle with the base at the top. The sacrum acts as a wedge between the two iliac bones of the pelvis and transmits the axial loading forces of the spine to the pelvis and lower extremities. The sacrum is rotated anteriorly with the superior endplate of the S1 vertebra angled from about 30 to about 60 degrees in the horizontal plane.

The S1 vertebra includes a spinous process aligned along a ridge called the medial sacral crest. However, the spinous process on the S1 vertebra may not be well defined and therefore not adequate for supporting an implant. One example of this dilemma is the inability of the spinous process to adequately support an interspinous process implant positioned between the L5 and S1 spinous processes.

SUMMARY

The present application is directed to devices that mount to the sacrum and methods of use. One embodiment of the device may include first and second anchors that mount to the sacrum, and first and second lateral extensions coupled to the anchors to secure the device to the sacrum. A bearing face having a width is positioned between the lateral extensions. The face may have a height in an anterior-posterior direction greater than the spinous process of the sacrum. Further, the bearing face may be oriented in a superior direction when the device is mounted to the sacrum.

An implant may be supported by the device to space the sacrum and L5 vertebra. The implant may be an interspinous device and positioned between the L5 spinous process and the bearing face. The implant is supported at least in part on the bearing face.

DETAILED DESCRIPTION

Figure 1:
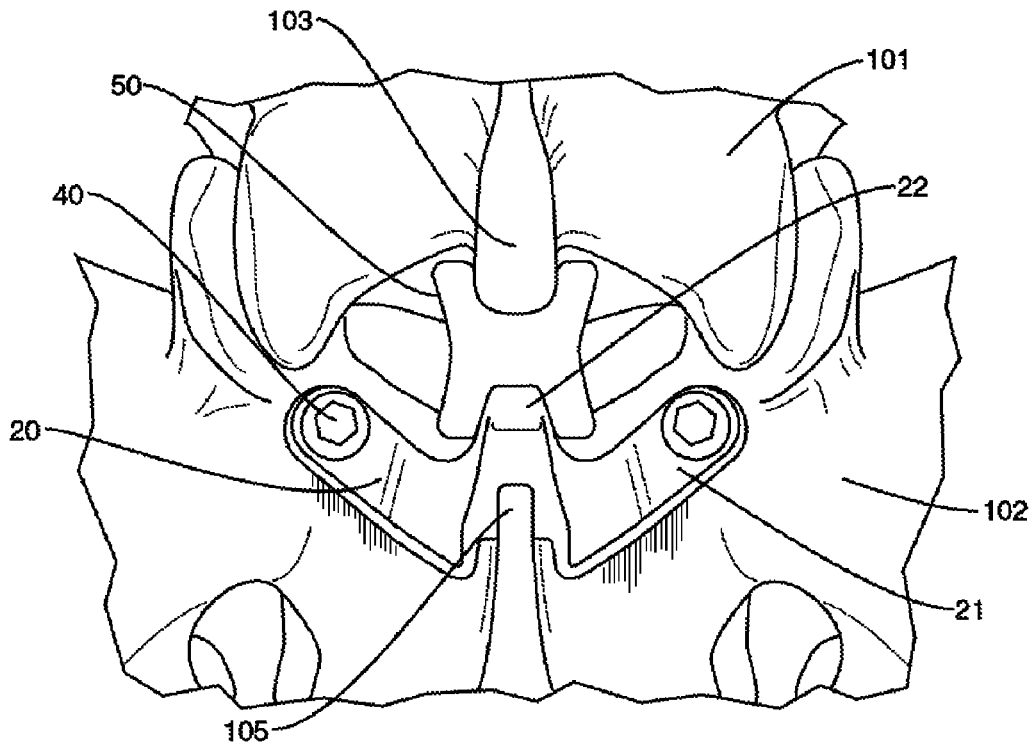
FIG. 1 is a rear view of a system having a base and an implant according to one embodiment.

The present application is directed to a base that attaches to the sacrum and includes a bearing face to support an implant. FIG. 1 illustrates one embodiment having a base 20 that attaches to the sacrum 102. A mount 22 extends posteriorly outward from the base 20 and is sized to contact an inferior portion of an implant 50. The implant 50 extends between the mount 22 and the spinous process 103 of the L5 vertebra 101.

Figure 2:
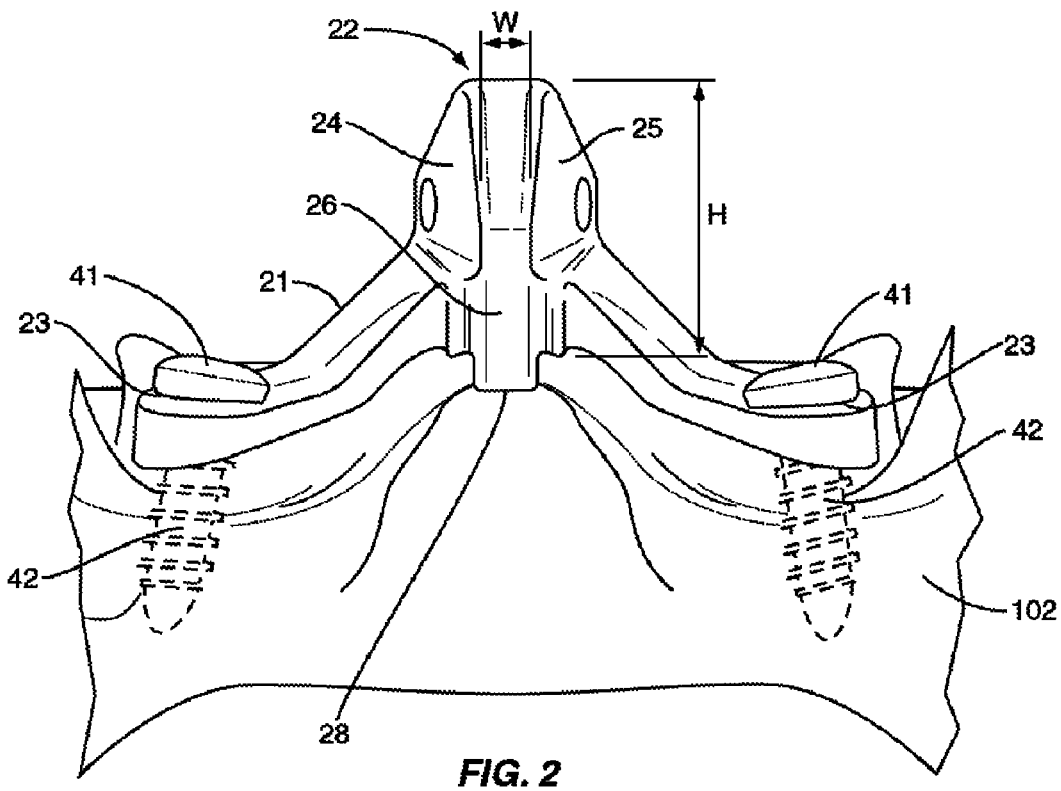
FIG. 2 is a top view of the base fastened to the sacrum according to one embodiment.
Figure 3:
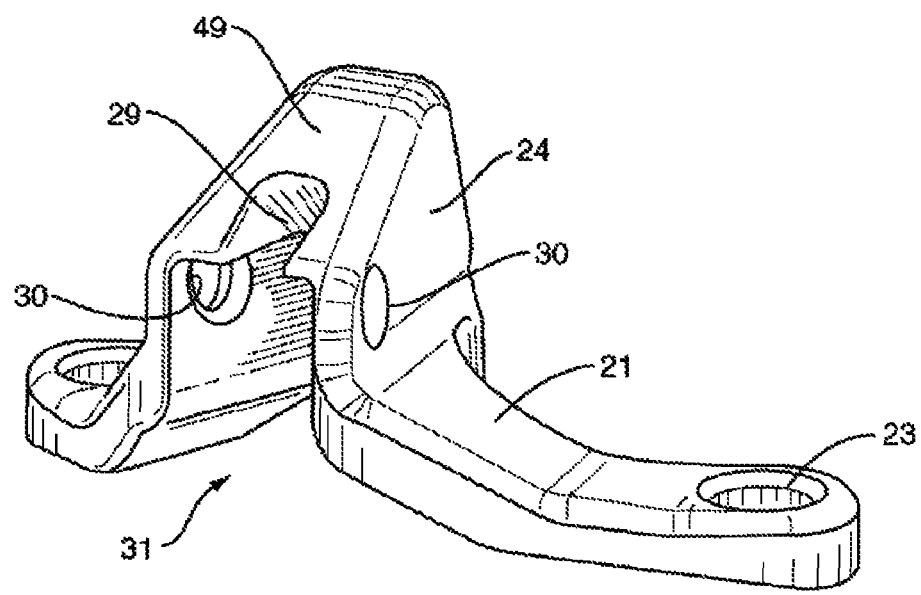
FIG. 3 is a perspective view illustrating an inferior portion of a base according to one embodiment.
Figure 4:
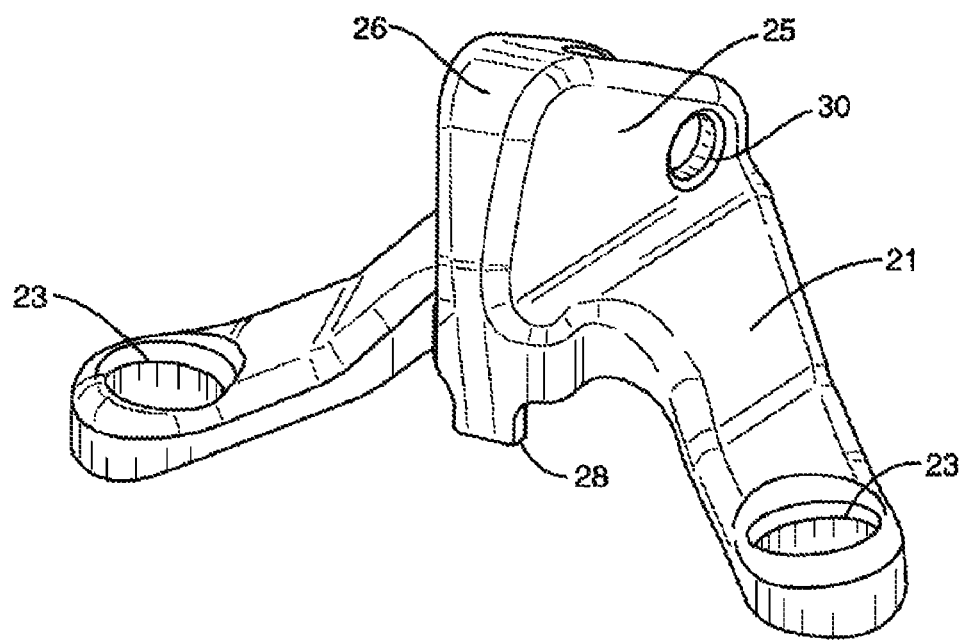
FIG. 4 is a perspective view illustrating a superior portion of a base according to one embodiment.

The base 20 includes the mount 22 and one or more extensions 21 as illustrated in FIGS. 2, 3, and 4. Mount 22 includes a bearing face 26 that faces in a superior direction when the base 20 is mounted to the sacrum 102. Bearing face 26 has a height H and width W to support the implant 50. The bearing face 26 has a height H in an anterior-posterior direction to extend posteriorly outward from the sacrum 102 a distance to support the implant 50. In one embodiment, the height H is greater than a height of the sacral spinous process 105. In one embodiment, the width W of the bearing face 26 is substantially constant along the height H. In another embodiment, the width W varies along the height H. Bearing face 26 may extend outward from the sacrum 102 at a variety of angles. In one embodiment, the width W of the bearing face 26 is substantially equal to a width of the L5 spinous process 103. Bearing surface 26 may be substantially planar, substantially curved, or include a combination having planar and curved sections.

Mount 22 further includes first and second sections 24, 25 that extend from the bearing face 26. Sections 24, 25 are positioned along lateral sides of the sacral spinous process 105 when the base 20 is mounted to the sacrum 102. Sections 24, 26 may have a length to extend outward and contact the sacrum 102, or may have a lesser length and be spaced from the sacrum 102 when the base 20 is mounted. An intermediate section 49 may extend inferiorly from the bearing face 26. Intermediate section 49 may have a width to extend between the first and second sections 24, 25. A recess 31 is formed on an underside of the mount 22 and is sized to extend over the entirety or a portion of the sacral spinous process 105. The embodiments of FIGS. 2, 3, and 4 illustrate the sections 24, 25, 26, 49 being substantially flat and connected together along ridges. Another embodiment features the sections 24, 25, 26, 49 formed of a continuous curved member with the sections not clearly definable by ridge lines. Apertures 30 may extend through the first and second sections 24, 25 for receiving a tether as will be described in more detail below. Apertures 30 may also be used for grasping the base 20 during insertion and positioning into the patient.

A superior edge of the bearing face 26 may include a lip 28 as illustrated in FIG. 2. Lip 28 aligns the mount 22 on the sacrum 102, and specifically aligns the mount 22 on the sacral lamina. In one embodiment, the height H of the bearing surface includes the lip 28. In one embodiment, the height H excludes the lip 28. Lip 28 may have the same width as the bearing face width W, or a different width. As illustrated in FIGS. 1 and 3, a notch 29 may be formed in an inferior edge of the intermediate section 49. Notch 29 is sized to accommodate the S1 spinous process 105 of the sacrum 102. In one embodiment, the lip 28 and notch 29 are centered about a centerline of the bearing face 26. In one embodiment, the centerline of the bearing face 26 is aligned with the medial sacral crest.

One or more extensions 21 extend outward from the mount 22 to contact the face of the sacrum 102. Extensions 21 may include one or more apertures 23 to receive an anchor 40 to connect the base 20 to the sacrum. In one embodiment as illustrated in FIG. 2, extensions 21 have a length to position the apertures 23 at the sacrum pedicles for good fastener fixation. In one embodiment, anchors 40 comprise a head 41 that contacts the edges of the aperture 23 and a shaft 42 that extends into the sacrum 102. In one embodiment as illustrated in FIG. 1, extensions 21 have a superior edge that is substantially aligned with the superior edge of the bearing face 26.

Figure 5:
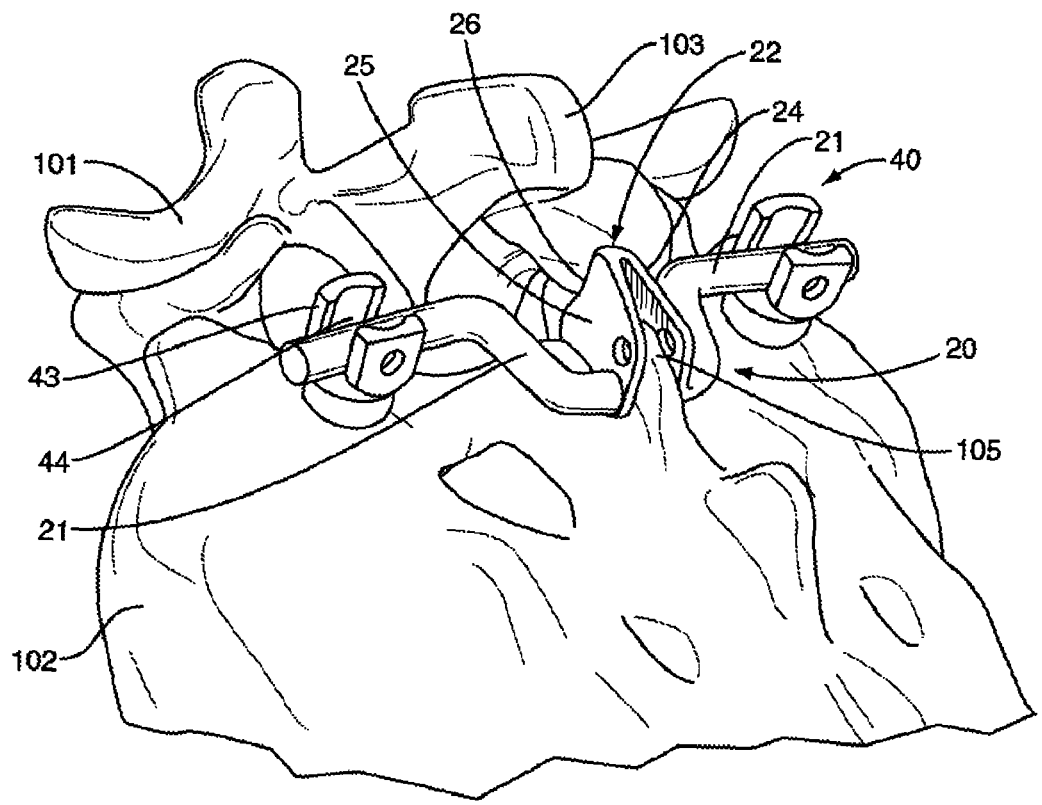
FIG. 5 is a perspective view of a base fastened to the sacrum by a pair of anchors according to one embodiment.
Figure 6:
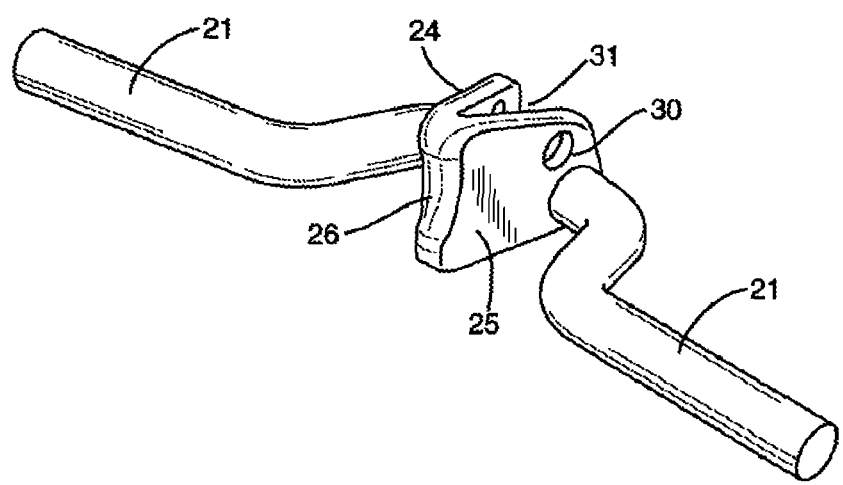
FIG. 6 is a perspective view illustrating a superior portion of a base according to one embodiment.

FIGS. 5 and 6 illustrate another embodiment of a base 20 comprising a mount 22 and extensions 21. For clarity, FIG. 5 does not include an implant 50 mounted between the L5 spinous process 103 and the mount 22. Mount 22 comprises first and second sections 24; 25 that connect together at a superior face that forms the bearing face 26. Bearing face 26 is positioned at the apex of the sections 24, 25 and is positioned on the superior face of the sacral spinous process 105. Bearing face 26 has a height H to extend outward from the sacrum 102 beyond the posterior edge of the sacral spinous process 105. Sections 24, 25 extend inferiorly outward from the bearing face 26 and are positioned along lateral edges of the spinous process 105. The sections 24, 25 further angle laterally outward in an inferior direction giving the mount 22 a substantially V-shape. In one embodiment, a height of the sections 24, 25 may be substantially equal to the height of the bearing face 26 as illustrated in FIG. 5. Bearing face 26 and sections 24, 25 form a recess 31 sized to fit over the spinous process 105. One or more apertures 30 may extend through the one or both sections 24, 25 to receive a tether.

Extensions 21 extend outward from the first and second sections 24, 25. In the embodiments illustrated, the extensions 21 extend from an inferior portion of the sections 24, 25, although other positions along the sections 24, 25 are also contemplated. Extensions 21 may be fixedly attached to the sections 24, 25 such that rotation of the extensions causes the mount 22 to also rotate. In another embodiment, the extensions 21 are movably connected to the sections 24, 25 and rotate independently from the sections.

One or more anchors 40 attach the extensions 21 to the sacrum 102. In this embodiment, anchors 40 are multi-axial devices comprising a saddle 43 that includes a channel 44 for receiving extensions 21. A threaded fastener (not illustrated) extends into an opening in the bottom of the channel 44. The connection between the fastener and saddle 43 provides for rotational movement of the saddle 43 to accommodate the extensions 21 at a variety of orientations. In one embodiment, extensions 21 have a circular cross-sectional shape that movably fits within the channel 44. The inner edges of the saddle 43 are threaded to receive a locking fastener (not illustrated) that extends over and locks the extensions 21 within the channel 44. A similar type of rotatable saddle connection is disclosed in U.S. Pat. No. 7,303,563 the relevant sections of which are herein incorporated by reference.

Figure 7:
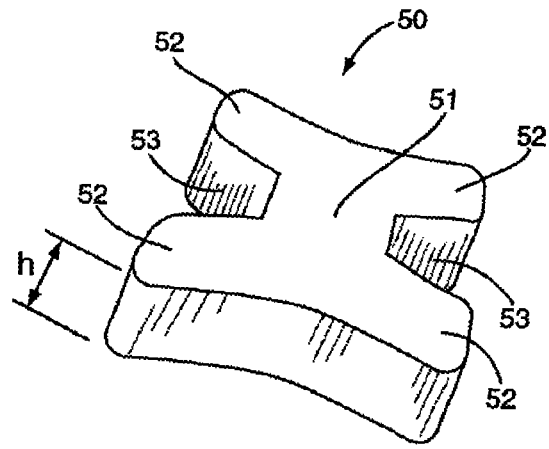
FIG. 7 is a perspective view of an implant according to one embodiment.

Implant 50 is an interspinous device sized to extend between the L5 spinous process 103 and the mount 22. One embodiment is illustrated in FIG. 7 and includes an interspinous section 51 and outwardly-extending arms 52. Inlets 53 are formed by the arms 52 on each side of the interspinous section 51. In one embodiment, an inferior surface of the interspinous section 51 contacts the bearing face 26 and a superior surface contacts the L5 spinous process 103. The inner edges of arms 52 may contact the first and second sections 24, 25 providing lateral support to the implant 50. In one embodiment, the height H of the bearing face 26 is greater than a height h of the implant 50. Implant 50 is constructed of a flexible material to dampen the relative movements during flexion and extension. Implant embodiments are disclosed in U.S. Patent Application Publication 2005/0261768 and U.S. Pat. No. 6,626,944 both herein incorporated by reference in their entirety. Another implant embodiment is the DIAM spinal stabilization device available from Medtronic Sofamor Danek of Memphis, Tenn.

In use, the base 20 is mounted to the sacrum 102. Initially, an incision is made to access the sacrum 102 and L5 vertebra 101. In one embodiment, the surface of the sacrum 102 including the sacral spinous process 105 is contoured such that the base 20 can be securely positioned on the sacrum 102. This may include contouring the superior surface of the spinous process 105 to reduce the height, or contouring a section of the medial sacral crest. In another embodiment, base 20 is positioned on the sacrum 102 without contouring.

The base 20 is positioned with the mount 22 extending outward in a posterior direction from the sacrum 102. The recess 31 is positioned to extend at least partially over the sacral spinous process 105. The bearing face 26 is positioned superiorly of the spinous process 105 and adjacent to the L5 spinous process 103. The mount 22 has a height H to extend beyond the spinous process 103 to provide a support for the implant 50. As illustrated in FIGS. 1 and 2, the notch 29 on the inferior edge of the mount 22 may extend over the spinous process 105 and the lip 28 aligns with the sacral lamina.

Once the mount 22 is situated over the sacral spinous process 105, anchors 40 connect the extensions 21 to the sacrum 102. One or more fasteners extend into the sacrum 102 to securely connect the base 20. In some embodiments, extensions 21 have a length to position the shaft 42 within the lamina, pedicles, sacral ala, or iliac crest of the sacrum 102.

Once the base 20 is mounted to the sacrum 102, interspinous implant 50 is inserted between the mount 22 and L5 spinous process 103. The inferior surface of the interspinous section 51 contacts the bearing face 26 and a superior surface faces the L5 spinous process 103. In one embodiment, the superior surface contacts the L5 spinous process 103. The inner edges of arms 52 may contact the first and second sections 24, 25 and the lateral edges of the spinous process 103 providing lateral support to the implant 50. A tether (not illustrated) may be used to more securely attach the implant 50 in position. Tether is attached to one or more of the apertures 30 within the mount 22, and may further extend around the spinous process 103 to maintain the implant within the interspinous space formed between the mount and L5 spinous process 103.

In one embodiment, the superior surface contacts the L5 spinous process 103. In another embodiment, the L5 spinous process 103 has been replaced with an implant. In this embodiment, the superior surface contacts the implant.

Figure 8:
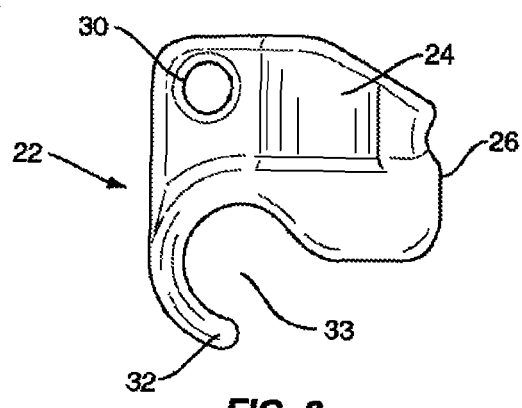
FIG. 8 is a side view of a mount according to one embodiment.
Figure 9:
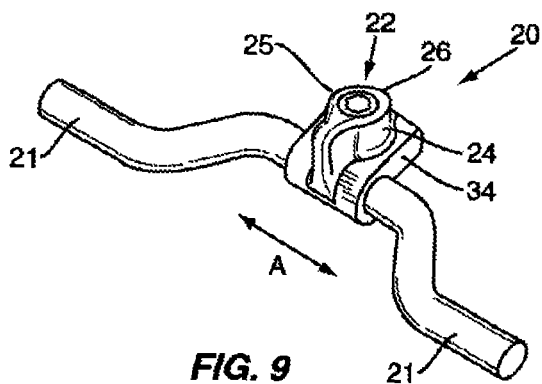
FIG. 9 is a perspective view of a base according to one embodiment.

The embodiments of the base 20 discussed above disclose the mount 22 and extensions 21 constructed in a unitary manner. Another embodiment features a modular design as illustrated in FIGS. 8 and 9 having a mount 22 that is detachable from the extensions 21. Mount 22 includes a hook 32 extending from an inferior section that forms a receiving area 33 sized to accommodate the extensions 21. Mount 22 further includes a superior bearing face 26 and lateral first and second sections 24, 25. Mount 22 may further extend outward from a base 34. Extension 21 has a shape to fit within the receiving area 33. The mount 22 may be movable along the extension 21 in the direction indicated by arrows A to position the mount 22 and accommodate differing anatomies between patients. A lock mechanism (not illustrated) may be associated with the mount 22 and/or extension 21 to prevent further movement once proper positioning is obtained. Anchors 40 attach the extension 21 to sacrum 102 as previously discussed.

Figure 10:
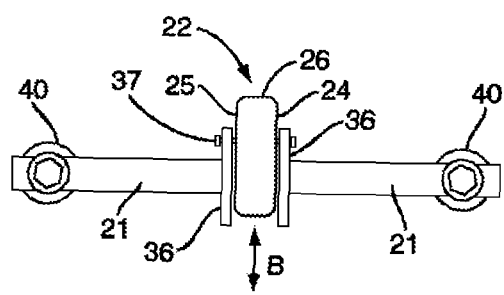
FIG. 10 is a top view of a base according to one embodiment.
Figure 11:
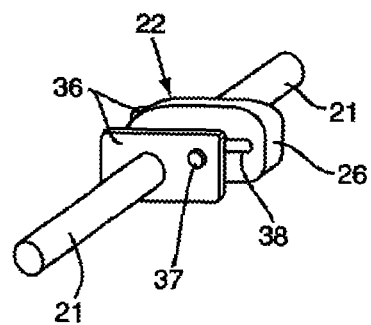
FIG. 11 is a perspective view of a base according to one embodiment.

FIGS. 10 and 11 illustrate another embodiment of the base 20 having a mount 22 positioned between extensions 21. Mount 22 includes a superior bearing face 26 having a width to support the implant 50. A slot 38 extends through the mount 22 between first and second sections 24, 25. Each extension 21 includes a platform 36 having an enlarged surface that aligns with a first and second section 24, 25 respectively. A member 37 extends between the platforms 36 and through the slot 38 to attach the mount 22 to the extensions 21. Mount 22 is vertically movable relative to the extensions 21 as indicated by arrows B. The extent of adjustment is controlled by the length of the slot 38. Movement of the mount 22 along the length of the slot 38 adjusts a distance between the bearing face 26 and the L5 spinous process 103. Slot 38 may further have a width to adjust a height of the mount in a posterior direction. Once the proper positioning is obtained, member 37 may be locked to prevent further movement. As with the other embodiments, anchors 40 attach the base 20 to the sacrum 102.

In one embodiment, mount 22 extends posteriorly beyond the height of the sacral spinous process 105. The mount may extend over part or an entirety of the spinous process 105. In another embodiment, mount 22 includes a bearing face 26 positioned on a superior face of the spinous process 105. In another embodiment, all or a portion of the spinous process 105 is removed during contouring prior to attachment of the base 20.

In one embodiment as illustrated in FIG. 1, base 20 is mounted to the sacrum 102 at a point relative to the S1 vertebra. In another embodiment, base 20 is mounted to the sacrum 102 relative to another vertebra, such as the S2 vertebra. In this embodiment, implant 50 has a greater length to extend between the L5 spinous process 103 and the bearing face 26 at the S2 vertebra.

Spatially relative terms such as "under", "below", "lower", "over", "upper", and the like, are used for ease of description to explain the positioning of one element relative to a second element, or relative to the anatomical elements of a patient. These terms are intended to encompass different orientations of the device in addition to different orientations than those depicted in the figures. Further, terms such as "first", "second", and the like, are also used to describe various elements, regions, sections, etc and are also not intended to be limiting. Like numbers refer to like elements throughout.

The present invention may be carried out in other specific ways than those herein set forth without departing from the scope and essential characteristics of the invention. Implants 50 may have a variety of shapes depending upon the context of usage. In one embodiment, a mid-line of the bearing face 26 is equally distanced between the extensions 21. In one embodiment, a single extension 21 extends from the mount 22. In one embodiment, the S1 spinous process has an initial height prior to mounting the device. The mount 22 has a height greater than the initial height. The present embodiments are, therefore, to be considered in all respects as illustrative and not restrictive, and all changes coming within the meaning and equivalency range of the appended claims are intended to be embraced therein.

What is claimed is:

1. A device to provide an inferior support for an interspinous implant between an L5 vertebra and a spinous process of a sacrum, the device comprising:
    first and second lateral extensions configured to be secured to the sacrum;
    a first section that extends outward in a posterior direction from the first lateral extension when the first lateral extension is mounted to the sacrum;
    a second section that extends outward in the posterior direction from the second lateral extension when the second lateral extension is mounted to the sacrum;
    a bearing face extending between the lateral extensions and connected to each of the first and second sections, the bearing face having a height in an anterior-posterior direction greater than the spinous process of the sacrum and oriented in a superior direction when the device is mounted to the sacrum to support the interspinous implant;
    a recess formed and enclosed on a superior side by the bearing face and on the lateral sides by the first and second faces, the recess including a first open side oriented in an anterior direction when the device is mounted to the sacrum to receive the spinous process of the sacrum and a second open side oriented in an inferior direction when the device is mounted to the sacrum, wherein the first open side and the second open side are in communication with each other;
    the bearing face having a width that is smaller than the second open side.

2. The device of claim 1, wherein the width of the bearing face is substantially constant along the height.

3. The device of claim 1, wherein the recess includes a tapered width measured between the first and second sections that increases from the superior side to the second open side.

4. The device of claim 1, wherein the bearing face is fixedly connected to the first and second extensions.

5. The device of claim 1, wherein a first terminal end of the first section farthest away from the bearing face defines a first edge of the second open side.

6. The device of claim 5, wherein a second terminal end of the second section farthest away from the bearing face defines a second edge of the second open side.

7. A device to provide an inferior support for an interspinous implant between an L5 and S1 vertebra comprising:
    a body comprising:
        a superior bearing face;
        a first lateral section extending from a first lateral edge of the superior bearing face;
        a second lateral section extending from a second lateral edge of the superior bearing face;
        a recess formed by the superior bearing face and the first and second lateral sections, the recess having enclosed superior, posterior and lateral sides and open anterior and inferior sides when the body of the interspinous implant is positioned on the S1 vertebra wherein the open anterior side and the open inferior side are in communication with each other;
    first and second extensions that extend outward from the first and second lateral sections and are sized to extend along a posterior face of the S1 vertebra, each of the first and second extensions including an aperture that aligns with the S1 vertebra;
    an inferior-most edge of the body defining an edge of the open anterior side;

the superior section positioned to be superior to the S1 spinous process and extend outward in a posterior direction when the device is mounted to the S1 vertebra to support the interspinous implant.

8. The device of claim 7, wherein the inferior-most edge of the body is formed by an exposed inferior terminal edge of one of the first and second lateral sections, the inferior terminal edge positioned on an opposite end of the lateral sidewall from the superior face.

9. The device of claim 7, wherein the first and second lateral sections each include a superior edge at the superior section and an exposed inferior edge that defines the open anterior side of the recess.

10. The device of claim 7, wherein the open anterior side of the recess includes a greater width than the superior section.

11. The device of claim 7, wherein the superior section has a substantially constant width measured perpendicular to a longitudinal axis of the recess.

12. The device of claim 7, wherein the enclosed posterior side of the recess includes a rounded corner that extends outward in a posterior direction from the superior section when the device is mounted to the S1 vertebra.

13. The device of claim 7, wherein the closed posterior side includes a first portion with a first width and a notch extending from the first portion and having a smaller width, the notch being in closer proximity to the superior face than the first portion.

14. The device of claim 13, wherein the notch is positioned between the first and second lateral sections.

15. A device to provide an inferior support for an interspinous implant between an L5 vertebra and a spinous process of a sacrum, the device comprising:

an intermediate section including
  a superior bearing face,
  first and second lateral sections that extend outward from the superior bearing face, and
  a posterior sidewall that extends between the first and second lateral sections and the superior bearing face, an open anterior side, an open inferior side, and an open posterior side, the intermediate section including a tapered width with the superior bearing face including a smaller width measured perpendicular to a longitudinal axis of the intermediate section than the open inferior side, wherein the open anterior side and the open inferior side are in communication with each other such that they form a recess between the superior bearing face and the first and second lateral sections;

a first extension that extends outward from the first lateral section and includes a first aperture being adapted to align with the sacrum; and a second extension that extends outward from the second lateral section and includes a second aperture being adapted to align with the sacrum.

16. The device of claim 15, wherein the open posterior side is formed between the first and second lateral sections that extend inferiorly beyond the posterior sidewall.

17. The device of claim 15, wherein the open anterior side forms a notch that extends towards the superior bearing face from the open posterior side, the notch including a smaller width measured perpendicular to the.

* * * * *